United States Patent
Seebach et al.

(10) Patent No.: US 10,154,892 B2
(45) Date of Patent: Dec. 18, 2018

(54) ARTIFICIAL SPHINCTER

(71) Applicant: DUALIS MEDTECH GMBH, Seefeld (DE)

(72) Inventors: Michael Seebach, München (DE); Marco Dudziak, Eltmann (DE); Sören Michel, Seefeld (DE); Christian Steer, München (DE)

(73) Assignee: DUALIS MEDTECH GMBH, Seefeld (DE)

( * ) Notice: Subject to any disclaimer, the term of this patent is extended or adjusted under 35 U.S.C. 154(b) by 223 days.

(21) Appl. No.: 14/424,865

(22) PCT Filed: Aug. 23, 2013

(86) PCT No.: PCT/EP2013/067544
§ 371 (c)(1),
(2) Date: Feb. 27, 2015

(87) PCT Pub. No.: WO2014/033062
PCT Pub. Date: Mar. 6, 2014

(65) Prior Publication Data
US 2015/0202034 A1    Jul. 23, 2015

(30) Foreign Application Priority Data

Aug. 28, 2012  (DE) .................. 10 2012 215 243

(51) Int. Cl.
*A61F 2/04*  (2013.01)
*A61F 2/00*  (2006.01)

(52) U.S. Cl.
CPC ........ *A61F 2/004* (2013.01); *A61F 2002/047* (2013.01); *A61F 2210/0057* (2013.01);
(Continued)

(58) Field of Classification Search
CPC ........ A61F 2/00; A61F 2/0004; A61F 2/0013; A61F 2/0027; A61F 2/0031;
(Continued)

(56) References Cited

U.S. PATENT DOCUMENTS

| 3,863,622 A | 2/1975 | Buuck |
| 2005/0240144 A1 | 10/2005 | Wassemann et al. |

(Continued)

FOREIGN PATENT DOCUMENTS

| DE | 19511998 A1 | 10/1996 |
| DE | 10013519 A1 | 10/2001 |
| WO | 0145488 A2 | 6/2001 |

OTHER PUBLICATIONS

Office Action of German priority patent application No. 10 2012 215 243.1 dated Nov. 25, 2015; 8 pgs.
(Continued)

*Primary Examiner* — Thaddeus B Cox
(74) *Attorney, Agent, or Firm* — Maier & Maier, PLLC

(57) ABSTRACT

The invention relates to an artificial sphincter for controllably occluding a urine-carrying vessel of an incontinent patient, including a first electrically driven pump for pumping the hydraulic fluid against the force produced by the inherent elasticity of the reservoir from the hydraulic occlusion device to the elastic reservoir during normal operation, and a second emergency pump for pumping the hydraulic fluid against the force produced by the inherent elasticity of the reservoir from the occlusion device to the elastic reservoir during emergency operation, namely when said first pump does not function properly. The invention further relates to a method for controlling an artificial sphincter.

10 Claims, 1 Drawing Sheet

(52) U.S. Cl.
CPC ............... *A61F 2230/0065* (2013.01); *A61F 2250/0001* (2013.01); *A61F 2250/0003* (2013.01)

(58) Field of Classification Search
CPC .......... A61F 2/0036; A61F 2/004; A61F 2/04; A61F 2/042; A61F 2250/0003; A61F 2002/047–2002/048; A61F 2230/0065
See application file for complete search history.

(56) References Cited

U.S. PATENT DOCUMENTS

| | | |
|---|---|---|
| 2010/0211175 A1 | 8/2010 | Gomez-Llorens |
| 2010/0256757 A1* | 10/2010 | Lima ........................ A61F 2/004 623/14.13 |
| 2011/0015738 A1* | 1/2011 | Vaingast ............... A61F 2/0036 623/14.13 |
| 2012/0157759 A1* | 6/2012 | Wirbisky ................ A61F 2/004 600/31 |

OTHER PUBLICATIONS

International Search Report and Written Opinion dated Nov. 14, 2013, in connection with corresponding International Application No. PCT/EP2013/067544 (13 pgs.).

\* cited by examiner

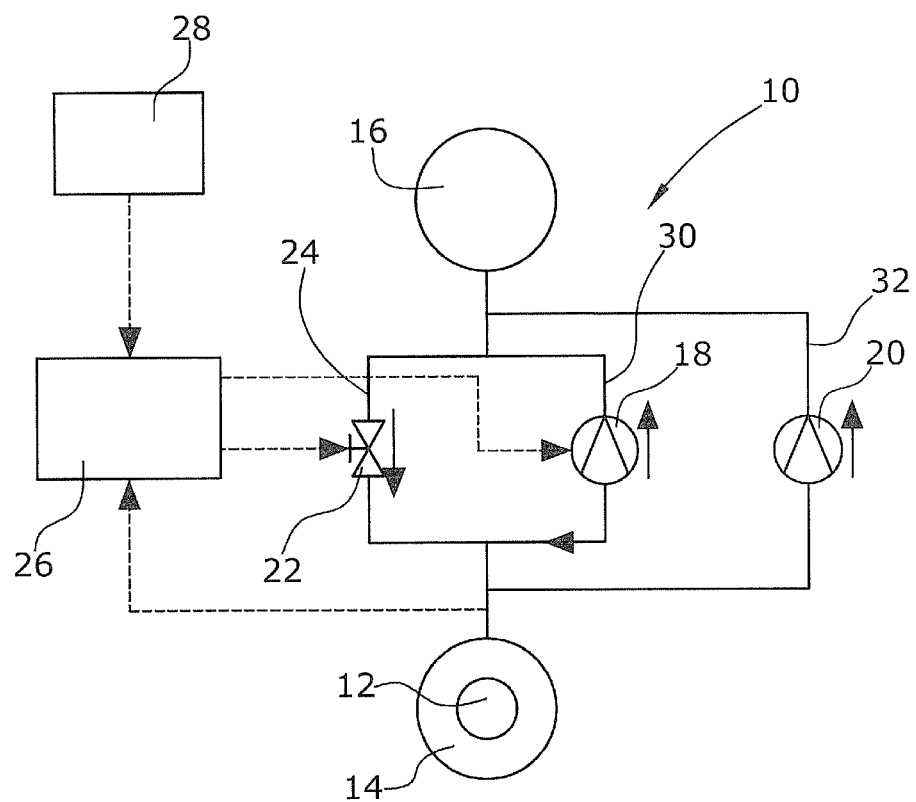

ARTIFICIAL SPHINCTER

The invention relates to an artificial sphincter for controllably occluding a urine-carrying vessel of an incontinent patient. The invention further relates to a method for controlling an artificial sphincter.

It is known to implant an artificial sphincter into incontinent patients. Such a system is offered by the American Medical System company under the trade name AMS 800, for example. This is a purely hydraulically actuated system where a hydraulically operated occlusion device is arranged around a urine-carrying vessel of the patient. The occlusion device is connected with a reservoir via a line. The occlusion device is filled with the hydraulic fluid from the reservoir and thus closes the urine-carrying vessel extending through said device. Between the reservoir and the occlusion device a manually operable pump is arranged which is implanted in the body of the patient such that it is adapted to be operated from outside. By operating this pump the hydraulic fluid is returned from the occlusion device into the reservoir i. e. the occlusion device is opened and the patient can empty his bladder.

The described system is disadvantageous in that is must be designed to as certain maximum pressure which is sufficient to reliably close the urine-carrying vessel even in so-called stress situations. A stress situation occurs when the pressure in the urine-carrying vessel increases due to different circumstances. This may happen when the patient coughs, sneezes or performs certain physical activities, for example. In such situations a temporary strong pressure increase may occur in the urine-carrying vessel. Even in such situations the urine-carrying vessel must be reliably closed by the artificial sphincter such that the described system requires a relatively high pressure to be constantly applied to the sphincter. Such a constant application of a high pressure to the urine-carrying vessel frequently leads to damage of the vessel by atrophy, for example.

Further, the described system can be adapted to changes in the body of the patient to a very limited extent only. Thus after an implantation it may be necessary to close the urine-carrying vessel at a higher or lower pressure than originally intended. Flexible matching of the closing pressure can be attained with the described system only by supply of an additional hydraulic fluid to the system via a port, for example. This requires the patient to be subjected to an invasive intervention.

It is an object of the invention to provide an artificial sphincter by means of which a urine-carrying vessel can be reliably closed even in stress situations, wherein the risk of a permanent damage of the urine-carrying vessel is minimized. The invention is further intended to provide a corresponding method for controlling an artificial sphincter.

According to the invention, the objects are achieved with the features of claims 1 and 7.

The artificial sphincter according to the invention serves for controllably occluding a urine-carrying vessel of an incontinent patient. The sphincter comprises an implantable, in particular annular hydraulic occlusion device which, when implanted, is arranged at the urine-carrying vessel such that during filling of the hydraulic occlusion device with a hydraulic fluid an occlusion of the urine-carrying vessel is performed. The latter can thus be closed by the occlusion device. For clearing the urine-carrying vessel the hydraulic occlusion device is adapted to be emptied.

The artificial sphincter comprises an implantable elastic reservoir which is in fluid communication with the occlusion device such that the hydraulic fluid can flow from the elastic reservoir towards the occlusion device and back. Here, the flow of the hydraulic fluid from the elastic reservoir to the hydraulic occlusion device is in particular exclusively caused by the inherent elasticity of the elastic reservoir. Thus no other components, in particular pumps, are provided by means of which the hydraulic fluid is delivered from the elastic reservoir towards the hydraulic occlusion device. If a fluid communication between the elastic reservoir and the occlusion device exists, the occlusion device is filled with hydraulic fluid such that it closes the urine-carrying vessel.

For the patient to be able to empty his bladder, the artificial sphincter according to the invention comprises a first electrically driven pump for pumping the hydraulic fluid against the force produced by the inherent elasticity of the elastic reservoir from the occlusion device to the elastic reservoir. This first electrically driven pump is actuated by the patient during normal operation in order to allow the patient to empty his bladder. Actuation may be performed via a remote control arranged outside the body or via a button at the pump to be operated by the patient, for example. Further, a remote control may be provided inside the body of the patient, e. g. an operating button arranged subcutaneously which can thus be readily operated by the patient. The operation of the electrically driven pump does not require any large effort on the part of the patient since he is not required to pump the hydraulic fluid against the inherent elasticity of the elastic reservoir out of the occlusion device by his own strength. The artificial sphincter according to the invention is thus in particular suitable for physically weak and older patients. During normal operation, i. e. when the first electric pump is functioning, no fine motor skills of the patient are thus required to operate the pump. In contrast, in the case of occlusion devices known from prior art a mechanical pump difficult to operate is implanted into the scrotum of the patient, for example. According to the invention, use is also possible in the case of paralyzed patients since the pump can be operated by other persons via the remote control.

Preferably, the artificial sphincter further comprises a second emergency pump which is also adapted to deliver the hydraulic fluid from the hydraulic occlusion device towards the elastic reservoir. This second emergency pump is provided for emergency operation, namely when the first pump does no longer function properly. When the first electric pump fails, for example, the patient can empty his bladder by operating the second emergency pump.

Preferably, the second emergency pump is arranged in parallel to the first electrical pump between the elastic reservoir and the hydraulic occlusion device. The emergency pump may be a mechanical or electric pump. The use of a mechanical pump as an emergency pump is preferred since the emergency pump is very rarely used.

The sphincter according to the invention offers the advantage that the maximum pressure in the hydraulic occlusion device need not always be identical with the pressure in the elastic reservoir. Thus it is possible to have a relatively high pressure in the elastic reservoir which can be supplied to the hydraulic occlusion device in stress situations to reliably close the urine-carrying vessel even in such situations. During standard operation, i. e. when there is no stress situation, a lower pressure may be supplied to the hydraulic occlusion device, which however suffices to reliably close the urine-carrying vessel during standard operation. To reach this standard pressure during standard operation, part of the hydraulic fluid may be delivered by the electric pump from the hydraulic occlusion device back to the elastic reservoir, for example. Depending on the quantity of the hydraulic fluid which is delivered back into the elastic reservoir, the pressure in the hydraulic occlusion device may be adjusted between the maximum pressure prevailing in the elastic reservoir and a pressureless state (i. e. that state in which the occlusion device is completely emptied).

The urine-carrying vessel to be closed is thus no continuously closed at the high pressure which is required to ensure reliable closing in stress situations. Thus damage of the urine-carrying vessel can be avoided.

It is preferred that the first electric pump is a monodirectional pump by means of which the hydraulic fluid is adapted to be delivered exclusively from the hydraulic occlusion device towards the elastic reservoir and not in the opposite direction. Use of a monodirectional pump is sufficient since delivering of the hydraulic fluid from the elastic reservoir towards the hydraulic occlusion device is preferably exclusively performed through the inherent elasticity of the elastic reservoir.

According to a preferred embodiment, the sphincter according to the invention comprises a controllable valve which is arranged at a hydraulic line, in particular in parallel to the first pump. This controllable valve serves for closing and clearing this hydraulic line in response to controlling the controllable valve by the control device. The hydraulic line adapted to be closed by the controllable valve extends between the elastic reservoir and the hydraulic occlusion device. By means of the illustrated controllable valve the hydraulic line between the elastic reservoir and the occlusion device can thus be optionally opened or closed. As a function of the operation of the controllable valve the amount of hydraulic fluid to be delivered from the reservoir to the occlusion device can thus be controlled. When the controllable valve is prematurely closed during the process of filling the occlusion device, a high pressure is not applied to the latter, for example. However, when the controllable valve is closed very late or not closed at all, a high pressure is applied to the occlusion device, which may possibly even correspond to the maximum pressure prevailing in the reservoir.

Preferably, the sphincter according to the invention further comprises a sensor for directly and/or indirectly sensing a pressure and/or pressure increase in the urine-carrying vessel. On the basis of the signals from the sensor the controllable valve and/or the first pump are controlled. When a sudden pressure increase in the urine-carrying vessel is detected by the sensor, for example, a stress situation may be assumed. For example, it is possible that the patient is coughing at this moment. In response to this sensed sudden pressure increase the controllable valve may be opened by the control device such that the hydraulic fluid in the elastic reservoir jerkily flows into the occlusion device. Thus the pressure prevailing in the occlusion device increases very rapidly such that the urine-carrying vessel can be reliably closed even in the present stress situation. The sensor may be a separate sensor which is arranged at the urine-carrying vessel, at the bladder or at any place in the peritoneum/abdomen, for example. Alternatively or additionally, it is possible to detect a pressure change directly at the hydraulic occlusion device. This is possible since a rapid pressure increase in the urine-carrying vessel results in a corresponding pressure change in the occlusion device. Thus an additional sensor is not necessary. In this embodiment, the hydraulic occlusion device proper is thus used as a sensor.

Irrespective of the type of sensor used it is possible to measure the absolute pressure in the urine-carrying vessel and/or a pressure increase, i. e. the change of the pressure over time. If exclusively a pressure increase is measured it is not necessary to determine the absolute pressure. Exclusively identifying a pressure increase which exceeds a certain limit value is sufficient for recognizing a stress situation and, on the basis thereof, increasing the pressure in the hydraulic occlusion device to the stress pressure.

A stress situation may be assumed when the abdominal pressure shows a pressure increase rate of more than 36 mm Hg/s, preferably 70 mm Hg/s and particularly preferably 110 mm Hg/s. The pressure increase rate can be determined through a CLP measurement, for example. For explanations see the following publication:

[1] Palmtag, Goepel, Heidler: Urodynamik, 2nd edition, p. 109 http://www.springerlink.com/content/978-3-540-72505-3/#section=319686&page=1

The illustrated pressure change rates may also be employed in a pressure measurement in other areas, at the bladder, for example, or via the pressure of the hydraulic occlusion device.

Further, a stress situation may be assumed when an abdominal pressure of 55 mm Hg is measured. A stress situation may be assumed when one of two criteria, namely an increased pressure change rate or an increased absolute abdominal pressure, is detected.

Detection of a stress situation through the stated limit pressures is reasonable when the sphincter according to the invention does not dynamically respond to any pressure change and in this case the pressure prevailing in the hydraulic occlusion device is matched at any time to the pressure prevailing in the biological system. In this embodiment, the pressure in the hydraulic occlusion system is exactly as high as required at the moment, even in a stress situation. Thus this is a continuous pressure regulation. Alternatively, as illustrated above, it is possible to detect a stress situation through the aforementioned criteria, and if such a situation is detected, to increase the pressure in the hydraulic occlusion system to a defined stress pressure irrespective of the actual stress pressure prevailing in the biological system. Preferably, in this embodiment, there are merely two states of the pressure in the hydraulic occlusion device, namely one for the normal situation (normal pressure) and one for any stress situation (stress pressure) which is independent of the actual stress pressure in the biological system. This offers the advantage that considerably less regulation is required and the pressure measurement in the biological system can be facilitated.

It is preferred that the second emergency pump comprises a deactivation mechanism such that the hydraulic line inside of which this emergency pump is located is blocked during normal operation. This means that no hydraulic fluid can flow through this hydraulic line such that during normal operation the hydraulic fluid merely flows through the first electric pump and possibly through the controllable valve.

Further, it is preferred that the first electric pump and the controllable valve each comprise a deactivation mechanism such that the two hydraulic lines inside of which the first electric pump and the controllable valve are located are adapted to be blocked in a case of emergency such that then the hydraulic fluid can be pumped by the second emergency pump from the hydraulic occlusion device to the reservoir without it flowing back to the occlusion device via the controllable valve or the first electric pump.

It is preferred that the passage volume of the controllable valve is adapted to be adjusted by opening the controllable valve to a larger or smaller extent, for example. This can be performed depending on the signals detected by the sensor.

It is further preferred that the control device is adapted to output a control command to fully open the controllable valve when the pressure detected by the sensor in the urine-carrying vessel exceeds a defined limit pressure. This results in a jerky filling of the hydraulic occlusion device with hydraulic fluid caused by the inherent elasticity of the elastic reservoir, until the same pressure level in the occlusion device and the reservoir is attained or until the controllable valve is closed again. Owing to the interaction of the controllable valve and the elastic reservoir the hydraulic occlusion device can be considerably more rapidly filled with hydraulic fluid in a stress situation than by use of an electric or manual pump for delivering the hydraulic fluid into the occlusion device. When a pump is used it cannot be ensured that the pressure sufficiently rapidly builds up in the occlusion device such that reliable closing of the urine-carrying vessel is not always attained in a stress situation.

Completely opening the controllable valve in a stress situation may lead to the pressure in the hydraulic occlusion device becoming higher than necessary. This may be due to the fact that by completely opening the controllable valve the pressure considerably more rapidly increases in the hydraulic occlusion device. Thus the pressure in the occlusion device is possible higher than required for reliably closing the urine-carrying vessel in the present stress situation. However, this does not result in a permanent damage of the urine-carrying vessel since a short time after the jerky filling of the occlusion device the latter may be partly emptied again by the first electric pump. This can also be carried out gradually such that a first emptying process is carried out up to a point where the occlusion device has reached the pressure which is required to reliably close the urine-carrying vessel in the present stress situation. In another step which may be performed a few minutes later, for example, it is possible to deliver further hydraulic fluid from the occlusion device by means of the electric pump such that the standard pressure is reached again which is sufficient for reliably closing the urine-carrying vessel during standard operation.

With the sphincter according to the invention it is further possible to very flexibly respond to individual demands of the patient. For example, the implantation of the system may result in anatomical changes in the body of the patient which require the urine-carrying vessel to be closed at a higher or lower pressure than originally intended. A change of the control of the controllable valve and/or the electric pump allows for very easily responding to such a demand.

The invention further relates to a method for controlling an artificial sphincter for controllably occluding a urine-carrying vessel of an incontinent patient. The method is in particular suitable for controlling an artificial sphincter as described in the present application. The method according to the invention comprises the following steps:

At first, a pressure and/or pressure increase in the urine-carrying vessel are directly or indirectly sensed by a sensor. This may be performed by arranging a pressure sensor or an expansion sensor directly at the urine-carrying vessel, for example. Alternatively or additionally, a pressure increase in the bladder of the patient can be sensed. This may also be performed by using a pressure or expansion sensor, for example. When measuring a pressure in the bladder it is also possible to determine the filling level in the bladder. Alternatively or additionally, a pressure measurement using pressure or expansion sensors may be performed at any place in the peritoneum or the abdomen.

Alternatively to direct sensing of the pressure and/or pressure increase using a sensor it is also possible to detect a pressure change at the occlusion device proper. When the pressure in the urine-carrying vessel increases, this pressure increase can also be measured at the occlusion device. For example, it is possible to measure a large pressure increase at the occlusion device. Thus stress situations can be recognized. It may also be possible to detect the filling level of the bladder.

A controllable valve which is arranged in a fluid line between an elastic reservoir and a hydraulic occlusion device is opened. This fluid line may be a very short fluid line. The controllable valve is opened when the pressure measured by the sensor exceeds a defined limit pressure. When the valve is opened the inherent elasticity of the elastic reservoir causes the hydraulic fluid to flow from the elastic reservoir to the hydraulic occlusion device until the same pressure level is reached in the occlusion device and the reservoir or the controllable valve is closed again.

The method according to the invention may comprise all features which have been described in conjunction with the device according to the invention, and vice versa.

It is preferred that the controllable valve is completely opened when the pressure sensed by the sensor exceeds the limit pressure. This results in a jerky filling of the hydraulic occlusion device with hydraulic fluid up to a stress pressure which is sufficient to reliably close the urine-carrying vessel during a stress situation.

In addition, it is preferred that after the jerky filling of the hydraulic occlusion device part of the hydraulic fluid is delivered back into the elastic reservoir by means of an in particular electrically driven pumping device.

In addition, it is preferred that the pressure in the hydraulic occlusion device is reduced to a standard pressure which is sufficient to reliably close the urine-carrying vessel during standard operation. Such a pressure reduction is performed after a stress situation, i. e. when there is no longer a stress situation.

It is possible to make both the standard pressure and the stress pressure dependent on the measured and/or derived pressure in the urine-carrying vessel.

For example, it is thus possible that the standard pressure is not always the same but is also adapted to different situations. Alternatively, it is possible to merely sense stress situations by detecting a rapid pressure increase in the urine-carrying vessel and to define a standard pressure for closing the urine-carrying vessel when there is no stress situation, for example. The latter is not changed during normal operation but could be changed by newly programming the sphincter according to the invention.

Hereunder a preferred embodiment of the invention is described with reference to the FIGURE.

The FIGURE shows a schematic diagram of the artificial sphincter according to the invention.

The artificial sphincter 10 comprises a hydraulic occlusion device 14 which is of an annular and preferably toroidal configuration and surrounds the urine-carrying vessel 12. The artificial sphincter 10 further comprises an elastic reservoir 16 which is connected with the hydraulic occlusion device 14 via a hydraulic line 24. In this hydraulic line 24 the controllable valve 22 is arranged which is controlled by the control device 26. This takes place in response to the signals sensed by the sensor 28. The sensor 28 in particular measures the pressure in the urine-carrying vessel 12. The control device 26 further controls the electric pump 18 which is arranged in a parallel hydraulic line 30. This hydraulic line 30 also extends from the elastic reservoir 16 to the hydraulic occlusion device 14 in a direction parallel to the hydraulic line 24.

Further, another hydraulic line 32 extends in parallel to these two lines, inside of which the second emergency pump 20 is arranged. When the first electric pump 18 does not operate properly, this pump can deliver the hydraulic fluid from the occlusion device 14 towards the elastic reservoir 16.

The passage volume of the controllable valve 22 is adapted to be adjusted by the control device 26. For example, it is thus possible to only partly open the control valve 22 when the pressure in the occlusion device 14 is intended to increase slowly. For example, this may be helpful when the closing pressure in the occlusion device 14 is to be adjusted as a function of the filling level of the bladder.

The energy supply of the overall system 10 can be ensured by a rechargeable battery not shown. Further, an inductive wireless energy transmission known in prior art is feasible.

The invention claimed is:

1. An artificial sphincter for controllably occluding a urine-carrying vessel of an incontinent patient, comprising:
 an implantable, in particular annular hydraulic occlusion device which, when implanted, is configured to be arranged at said urine-carrying vessel such that during filling of said hydraulic occlusion device with a hydraulic fluid said urine-carrying vessel is occluded and said hydraulic occlusion device is adapted to be emptied again for clearing said urine-carrying vessel, and
 an implantable elastic reservoir which is in fluid communication with said hydraulic occlusion device such that the hydraulic fluid can flow from said elastic reservoir towards said hydraulic occlusion device and back, wherein the flow of the hydraulic fluid from said elastic reservoir to said hydraulic occlusion device is caused by an inherent elasticity of said elastic reservoir, further comprising:
 a first electrically driven pump for pumping the hydraulic fluid against a force produced by the inherent elasticity of said reservoir from said hydraulic occlusion device to said elastic reservoir during normal operation,
 a controllable valve which is arranged in parallel to the first pump, at a hydraulic line between the elastic reservoir and the hydraulic occlusion device for closing and clearing said hydraulic line in response to control of said controllable valve by a control device, wherein the control device is configured to output a control command for completely opening the controllable valve when a pressure in the urine-carrying vessel sensed by a sensor exceeds a defined limit pressure such that due to the inherent elasticity of the elastic reservoir a jerky filling of the hydraulic occlusion device with hydraulic fluid is performed until said hydraulic occlusion device and said reservoir have reached a same pressure level or said controllable valve is closed again.

2. The artificial sphincter according to claim 1, wherein the first pump is a monodirectional pump through which the hydraulic fluid is adapted to be exclusively delivered from the hydraulic occlusion device towards the elastic reservoir and not in the opposite direction.

3. The artificial sphincter according to claim 1, wherein the sensor directly and/or indirectly senses the pressure and/or pressure increase in the urine-carrying vessel, wherein, on the basis of one or more signals from said sensor, control of the controllable valve and/or the first pump is performed.

4. The artificial sphincter according to claim 3, wherein a passage volume of the controllable valve is adapted to be adjusted as a function of the one or more signals.

5. A method for controlling an artificial sphincter for controllably occluding a urine-carrying vessel of an incontinent patient, in particular for operating an artificial sphincter according to claim 1, comprising:
 directly or indirectly sensing a pressure and/or pressure increase in a urine-carrying vessel by a sensor,
 opening a controllable valve which is arranged in a fluid line between an elastic reservoir and a hydraulic occlusion device, wherein opening is performed when the pressure measured by said sensor exceeds a defined limit pressure,
 wherein during opening of said valve the inherent elasticity of said elastic reservoir causes the hydraulic fluid to flow from said elastic reservoir to said hydraulic device until said hydraulic occlusion device and said reservoir have reached the same pressure level or said controllable valve is closed again.

6. The method according to claim 5, wherein the controllable valve is completely opened when the pressure measured by the sensor exceeds the limit pressure such that a jerky filling of the hydraulic occlusion device with hydraulic fluid up to a stress pressure is performed which is sufficient to reliably close the urine-carrying vessel during a stress situation.

7. The method according to claim 6, wherein after the jerky filling of the hydraulic occlusion device part of the hydraulic fluid is delivered back into the elastic reservoir in particular by an electrically driven pumping device.

8. The method according to claim 7, wherein the pressure in the hydraulic occlusion device is reduced to a standard pressure which is sufficient to reliably close the urine-carrying vessel during standard operation.

9. The method according to claim 5, wherein the controllable valve is completely opened when the pressure in the urine-carrying vessel sensed by the sensor exceeds a defined limit pressure such that due to the inherent elasticity of the elastic reservoir a jerky filling of the hydraulic occlusion device with hydraulic fluid is performed until said hydraulic occlusion device and said elastic reservoir have reached a same pressure level or said controllable valve is closed again.

10. The artificial sphincter according to claim 1, further comprising:
 a second emergency pump for pumping the hydraulic fluid against the force produced by the inherent elasticity of said reservoir from said hydraulic occlusion device to said elastic reservoir during emergency operation, namely when said first pump does not function properly.

* * * * *